United States Patent [19]

Krapcho

[11] B 3,984,405

[45] Oct. 5, 1976

[54] ANTI-INFLAMMATORY AGENTS
[75] Inventor: John Krapcho, Somerset, N.J.
[73] Assignee: E. R. Squibb & Sons, Inc., Princeton, N.J.
[22] Filed: Apr. 5, 1973
[21] Appl. No.: 348,433
[44] Published under the second Trial Voluntary Protest Program on February 3, 1976 as document No. B 348,433.

Related U.S. Application Data
[62] Division of Ser. No. 157,678, June 28, 1971, Pat. No. 3,767,653.

[30] Foreign Application Priority Data
May 26, 1972  Canada .............................. 143149

[52] U.S. Cl. ........................ 260/244 R; 260/243 B; 424/248
[51] Int. Cl.² ........................................ C07D 498/04
[58] Field of Search .................................. 260/244

[56] References Cited
UNITED STATES PATENTS
3,715,353  2/1973  Krapcho ............................ 260/244

Primary Examiner—Harry I. Moatz
Attorney, Agent, or Firm—Lawrence S. Levinson; Merle J. Smith; Burton Rodney

[57] ABSTRACT
Anti-inflammatory agents of the formula

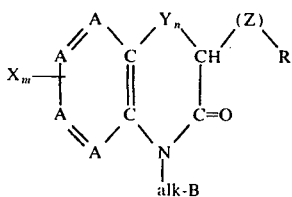

wherein X may be hydrogen, halogen, alkyl, haloalkyl, haloalkoxy, haloalkylthio, alkoxy, hydroxy, alkylthio, nitro, alkylsulfonyl, amino, alkanoylamino, or mono- or dialkylamino wherein any of the foregoing alkyl or substituted alkyl radicals contain up to 8 carbon atoms; m may be 0, 1, 2, 3 or 4; each A may be carbon, but one A may be nitrogen in any position provided n is 1; Y may be sulfur, sulfoxide, sulfonyl, or oxygen; n may be 0 or 1; R may be a straight or branched alkyl of up to 8 carbon atoms, cycloalkyl of from 3 to 8 carbon atoms; X-substituted phenyl, pyridyl, thienyl, furyl, naphthyl, alkylphenyl or alkenylphenyl wherein the alkyl or alkenyl radical may contain up to 4 carbon atoms either straight chain or branched; Z may be

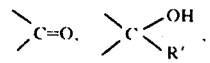

wherein R' is hydrogen, vinyl, allyl or R, or

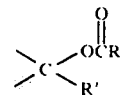

alk may be a straight or branched carbon chain of up to 6 carbon atoms; and B may be a basic nitrogen-containing radical; and pharmaceutically acceptable acid-addition salts thereof; N-oxides and pharmaceutically acceptable acid-addition salts thereof, and quaternary ammonium salts thereof.

2 Claims, No Drawings

ANTI-INFLAMMATORY AGENTS

RELATED APPLICATIONS

This application is a division of copending application Ser. No. 157,678, filed June 28, 1971 by John Krapcho and entitled Anti-inflammatory Agents, now U.S. Pat. 3,767,653.

OBJECTS OF THE INVENTION

It is an object of the present invention to provide new compounds having anti-inflammatory activity. Another object is to provide a method for the preparation of these compounds. A further object is to provide dosage forms containing the compounds of the invention. Yet another object is to provide a method for treating inflammatory conditions by administering the compounds of the invention. These and other objects of the present invention will be apparent from the following description.

DETAILED DESCRIPTION

The compounds of the present invention may be prepared according to the following reaction sequence wherein X, $m$, A, Y, $n$, alk, B, and R are as defined previously:

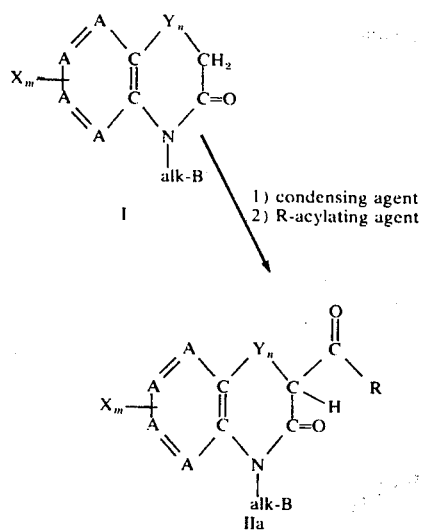

As condensing agent there may be employed such materials as, e.g., NaH, NaOCH$_3$, butyl Li, or K-t-butoxide.

The acylating agent may be an acyl halide,

or an ester of the formula

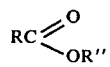

wherein R is as defined previously, hal is halogen and R'' is an organic radical, preferably a lower alkyl radical, e.g., methyl.

The acylation of the compound of formula I to form the corresponding compound of formula IIa takes place in a polar solvent such as, e.g., dimethylsulfoxide, tetrahydrofuran or ethyl acetate in the presence of a condensing agent. The reaction is exothermic and cooling may be necessary to keep the reaction below about 30°. When the reaction is completed, the mixture is heated to moderately elevated temperature of from about 50° to about 75° for from about 0.5 hour to about 4 hours, preferably from about 1.5 hours to about 2.5 hours. The pH of the resulting solution is then adjusted to from about 8.5 to about 9.5 to yield the compound of formula IIa as a precipitate which is then purified by solvent and aqueous extraction and crystallization.

Compounds of formula IIa may be converted to the corresponding secondary alcohol (IIb) by treatment with a reducing agent such as, for example, NaBH$_4$ or LiAlH$_4$, Na isopropoxide or catalytically using, e.g., Pd on carbon, while the corresponding tertiary alcohol (IIc) may be obtained by reaction of the compound of formula IIa with a Grignard reagent, R'Mghal, wherein R' and hal are as previously defined.

The hydroxyl group of the compounds of formula IIb and IIc may be esterified, for example, by use of an acid anhydride or an acyl halide or alkanoic acids of the formula

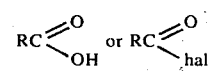

wherein R and hal are as previously defined.

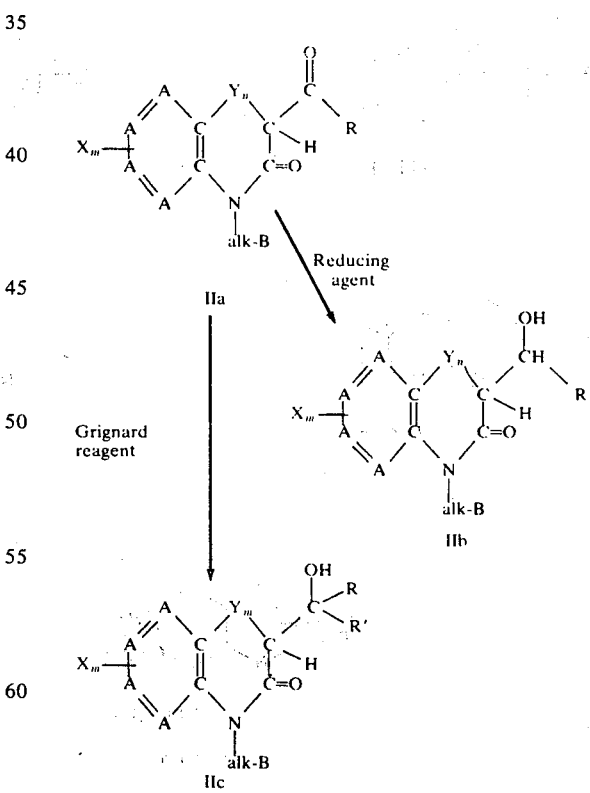

Specific types of compounds of formula I are the following:

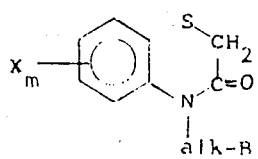

I-1

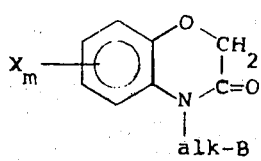

I-2

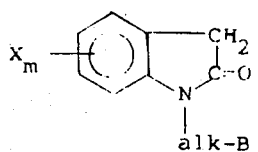

I-3

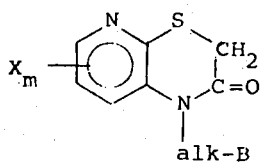

I-4

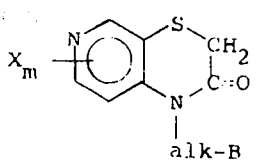

I-5

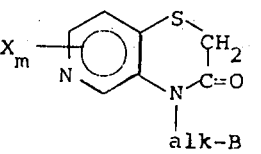

I-6

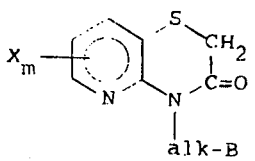

I-7

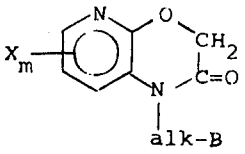

I-8

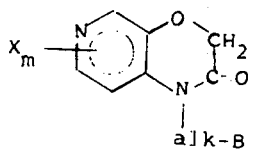

I-9

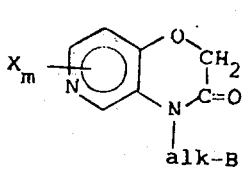

I-10

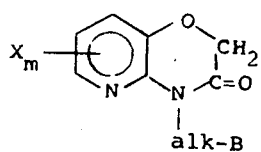

I-11

Compounds of formula IIa, IIb or IIc which are derived from the foregoing compounds of formula I will be further designated as IIa-1, IIa-2, IIa-3, etc., wherein the arabic numeral indicates the type of compound of formula I from which it may be prepared.

A. When Y is sulfur and each A is carbon, the compounds of formula II may be prepared by reacting an o-aminobenzenethiol or an $X_m$-substituted o-aminobenzenethiol of formula III with a halo-acetic acid, and reacting the resulting thiazinone of formula IV with a haloalkylene-B compound to yield a compound of formula I-1. The latter compound is then treated with a condensing agent and with an acylating agent to yield the corresponding compound of formula II-1. The compound of formula IIa-1 may be converted to the corresponding compound of formula IIb or IIc as described above.

5-n-propoxy-2-aminobenzenethiol;
5-n-hexyloxy-2-aminobenzenethiol;
4-ethylthio-2-aminobenzenethiol;
4-(trifluoromethyl)-2-aminobenzenethiol;
5-(trifluoromethyl)-2-aminobenzenethiol;
6-(trifluoromethyl)-2-aminobenzenethiol;
5-(trifluoromethoxy)-2-aminobenzenethiol;

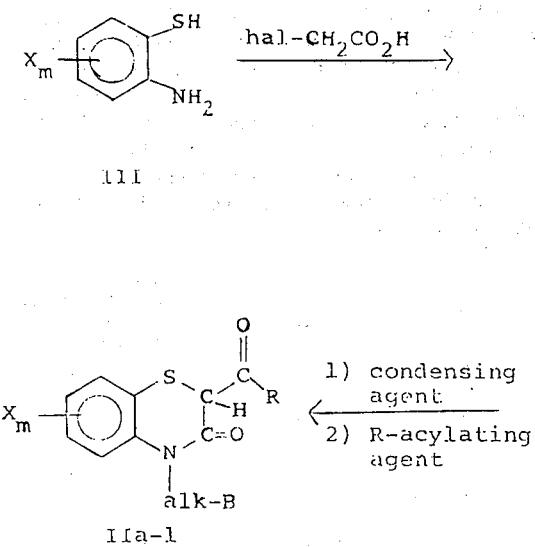

Examples of suitable o-aminobenzenethiols which may be used as starting material in the foregoing reaction sequence are the following:
2-aminobenzenethiol;
4-fluoro-2-aminobenzenethiol;
5-fluoro-2-aminobenzenethiol;
3,5,6-trifluoro-2-aminobenzenethiol;
3,4,5,6-tetrafluoro-2-aminobenzenethiol;
4-chloro-2-aminobenzenethiol;
5-chloro-2-aminobenzenethiol;
6-chloro-2-aminobenzenethiol;
5-bromo-2-aminobenzenethiol;
5-methyl-2-aminobenzenethiol;
6-methyl-2-aminobenzenethiol;
5-ethyl-2-aminobenzenethiol;
5-n-propyl-2-aminobenzenethiol;
5-n-hexyl-2-aminobenzenethiol;
3-hydroxy-2-aminobenzenethiol;
5-methoxy-2-aminobenzenethiol;
3,4-dimethoxy-2-aminobenzenethiol;
5-ethoxy-2-aminobenzenethiol;

4-(trifluoromethylmercapto)-2-aminobenzenethiol;
5-(trifluoromethylmercapto)-2-aminobenzenethiol;
5-nitro-2-aminobenzenethiol;
6-nitro-2-aminobenzenethiol;
2,4-diamino-5-methylthiophenol;
5-dimethylamino-2-aminobenzenethiol;
4-methylsulfonyl-2-aminobenzenethiol;

B. When Y is oxygen, and each A is carbon, the compounds of formula II may be prepared by reacting an o-nitrophenol or an $X_m$-substituted o-nitrophenol of formula V with a haloacetic acid followed by reduction of the nitro group to an amino group. Cyclization takes place spontaneously following reduction to yield a compound of formula VI. Reaction of the oxazinone compound of formula VI with a haloalkylene-B compound yields a compound of formula I-2. The latter compound is then treated with a condensing agent and with an acylating agent to yield the corresponding compound of formula IIa-2. The compound of formula IIa-2 may be converted to the corresponding compound of formula IIb or IIc as described previously.

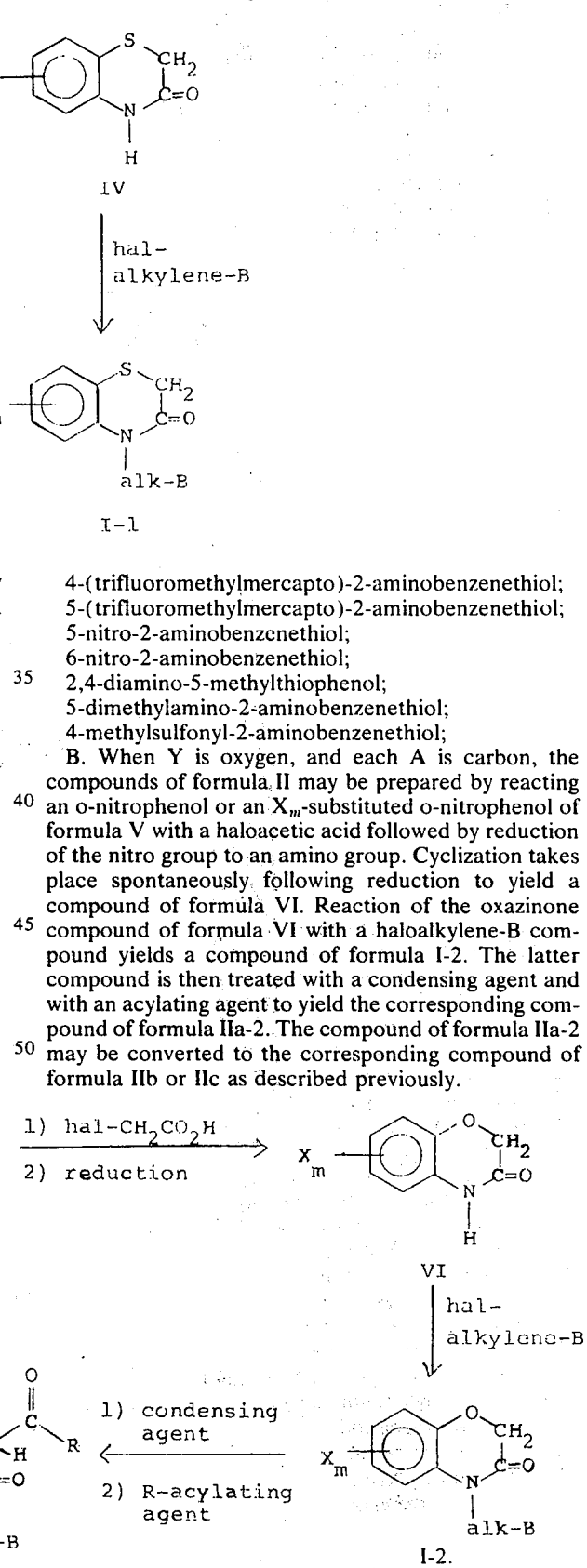

Suitable o-nitrophenols which may be used as starting material in the foregoing reaction sequence are the following:

2-nitrophenol;
2-nitro-4-chlorophenol;
2-nitro-4,6-dichlorophenol;
2-nitro-3,4,5,6-tetrachlorophenol;
2-nitro-4-bromophenol;
2-nitro-3,5-dibromophenol;
2-nitro-5-trifluoromethoxyphenol;
2-nitro-4-ethylthiophenol;
2-nitro-4,6-dibromophenol;
2,4-dinitrophenol;
2,5-dinitrophenol;
2,6-dinitrophenol;
2,4-dinitro-6-chlorophenol;
2,5-dinitro-4-chlorophenol;
2,6-dinitro-4-chlorophenol;
2,4-dinitro-6-bromophenol;
2,6-dinitro-4-bromophenol;
2,4,6-trinitrophenol;
2-nitro-6-methylphenol;
2-nitro-4-bromo-6-methylphenol;
2,4-dinitro-6-methylphenol;
2-nitro-3-methylphenol;
2-nitro-4-methylphenol;
2-nitro-5-methylphenol;
2,4-6-trinitro-5-methylphenol;
2-nitro-4-methyl-6-chlorophenol;
2-nitro-4-methyl-6-bromophenol;
2,5-dinitro-4-methylphenol;
2,6-dinitro-4-methylphenol;
2-nitro-4,5-dimethylphenol;
2-nitro-4,6-dimethylphenol;
2-nitro-3,4,6-trimethylphenol;
2,4-dinitro-3-i-propyl-6-methylphenol;
2-nitro-4-methylaminophenol;
2-nitro-5-chlorophenol;
2-nitro-5-fluorophenol;
2-nitro-4-fluorophenol;
2-nitro-5-bromophenol;
2-nitro-4-methylsulfonylphenol;
2-nitro-5-dimethylaminophenol;
2-nitro-5-ethylphenol;
2-nitro-5-n-hexylphenol;
2-nitro-5-methoxyphenol;
2-nitro-5-ethoxyphenol;
2-nitro-5n-hexyloxyphenol;
2-nitro-5-(trifluoromethyl)phenol.

C. When $n$ is 0, the compounds of formula II may be prepared by reacting an $X_m$-substituted dihydroindolone of formula VII with a haloalkylene-B compound to yield a compound of formula I-3. The latter compound is then treated with a condensing agent and with an acylating agent to yield the corresponding compound of formula IIa-3 which in turn may be converted to the corresponding compound of formula IIb or IIc as described previously.

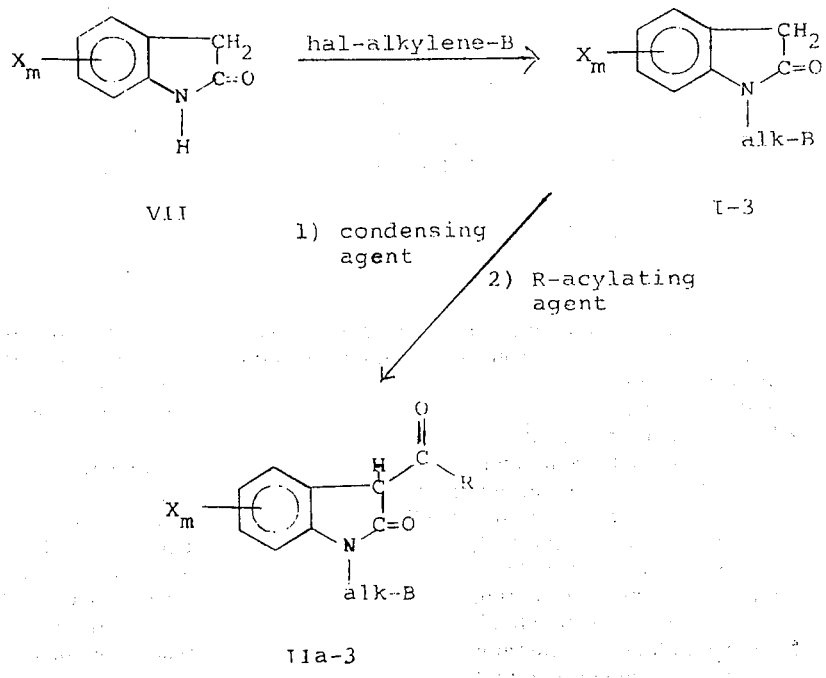

The dihydroindolone may be prepared by reacting aniline or an $X_m$-substituted aniline with α-chloroacetic acid, and treating the resulting amide with $AlCl_3$ (Friedel-Crafts reaction) to effect ring closure. Examples of suitable substituted anilines which may be used as starting materials in the foregoing reaction sequence are the following:

2-methylaniline (o-toluidine), 3-methylaniline (m-toluidine), 4-methylaniline (p-toluidine), 2,3-dimethylaniline, 2,4-dimethylaniline, 2,5-dimethylaniline, 3,4-dimethylaniline, 3,5-dimethylaniline, 2-ethylaniline, 2-isopropylaniline, 4-n-butylaniline, 4-t-butylaniline, 2-fluoroaniline, 3-fluoroaniline, 4-fluoroaniline, 2-chloroaniline, 3-chloroaniline, 4-chloroaniline, 2-bromoaniline, 3-bromoaniline, 4-bromoaniline, 2-iodoaniline, 3-iodoaniline, 4-iodoaniline, 2,3-dichloroaniline, 2,4-dichloroaniline, 2,5-dichloroaniline, 3,4-dichloroaniline, 3,5-dichloroaniline, 2,3-dibromoaniline, 3,4-dibromoaniline, 3,5-dibromoaniline, 2,4-diiodoaniline, 2-methyl-3-chloroaniline, 2-methyl-4-chloroaniline, 2-methyl-4-bromoaniline, 2-chloro-4-methylaniline, 3-chloro-4-methylaniline, 2-bromo-4-methylaniline, 2-methoxyaniline, 4-methoxyaniline, 3,5-dimethoxyaniline, 4-ethoxyaniline, 2-chloro-5-methoxyaniline, 2-nitroaniline, 3-nitroaniline, 4-nitroaniline, 2,4-dinitroaniline, 2-nitro-4-chloroaniline, 3-nitro-4-chloroaniline, 2-chloro-4-nitroaniline, 2-chloro-5-nitroaniline, 2-bromo-4-nitroaniline, 2-nitro-4,5-dichloroaniline, 2,4-dinitro-5-chloroaniline, 2,4-dinitro-5-bromoaniline, 2,4-dinitro-3-methylaniline, 2,4-dinitro-5-methylaniline, 4-dimethylaminoaniline, 3-trifluoromethylaniline, 2-trifluoromethyl-4-nitroaniline, 2-nitro-4-trifluoromethylaniline, 2-methoxy-4-methylmercaptoaniline, 2-methylmercapto-4-methoxyaniline, 4-(n-butylsulfonyl)-2-aminoanisole, 4-(ethylsulfonyl)-2-aminoanisole, 2-ethylsulfonyl-5-trifluoromethylaniline, and 2-methoxy-4-ethylsulfonylaniline.

D. When Y is sulfur and one A may be nitrogen, the compounds of formula II may be prepared by substituting for the thiazinone in paragraph A above one of the following compounds or an $X_m$-substituted derivative thereof;

| Type of Compound of Formula I | |
|---|---|
| I-4 | 1H-pyrido[2,3-b][1,4]-thiazin-2(3H)-one |
| I-5 | 1H-pyrido[3,4-b][1,4]-thiazin-2(3H)-one |
| I-6 | 1H-pyrido[4,3-b][1,4]-thiazin-2(3H)-one |
| I-7 | 1H-pyrido[3,2-b][1,4]-thiazin-2(3H)-one |

The pyridyl compounds of formula I-4, I-5, I-6 and I-7 may be prepared in an analogous manner to the benzothiazines of formula I-1 by starting from an aminopyridylthiol or an $X_m$-substituted aminopyridylthiol in palce of an o-aminobenzenethiol.

E. When Y is oxygen and one A may be nitrogen, the compounds of formula II may be prepared by substituting for the oxazinone in paragraph B above one of the following compounds or an $X_m$-substituted derivative thereof;

| Type of Compound of Formula I | |
|---|---|
| I-11 | 2H-pyrido[3,2-b][1,4]-oxazin-3(4H)-one |
| I-8 | 2H-pyrido[2,3-b][1,4]-oxazin-3(4H)-one |
| I-9 | 2H-pyrido[3,4-b][1,4]-oxazin-3(4H)-one |
| I-10 | 2H-pyrido[4,3-b][1,4]-oxazin-3(4H)-one |

The pyridyl compounds of formula I-8, I-9, I-10 and I-11 may be prepared in an analogous manner to the benzoxazines of formula I-2 by starting from a hydroxy nitropyridine or an $X_m$-substituted hydroxynitropyridine in place of an o-nitrophenol.

F. When Y is sulfur, the sulfoxide or sulfonyl compounds of formula II may be prepared by oxidizing the bivalent sulfur to the corresponding sulfoxide or sulfonyl. The techniques for such oxidations involve the use of $H_2O_2$ and $KMnO_4$, respectively, and are well known in the art. Alternatively, there may be employed a chloroform solution containing m-chloroperbenzoic acid. The sulfoxide of a compound of formula IIa may be obtained by treating a compound of formula IIa for from about 2 to about 24 hours at room temperature with one equivalent of m-chloroperbenzoic acid; the sulfone of a compound of formula IIa may be obtained by treating one of the bivalent sulfur compounds with two equivalents of m-chloroperbenzoic acid for the same time at room temperature, or for a shorter time with slight heating.

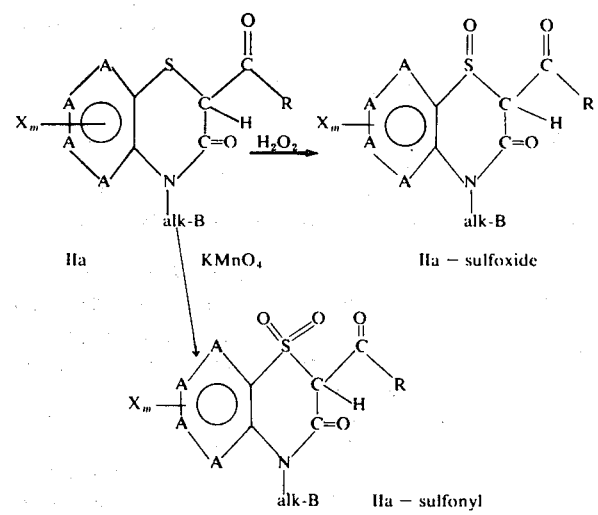

The alkyl radical alk may be a straight or branched carbon chain of up to 6 carbon atoms. Examples of such radicals are the following: methyl, ethyl, n-propyl, i-propyl, n-butyl, i-butyl, t-butyl, n-pentyl, 2-methyl-n-butyl, neopentyl, n-hexyl, 2-methyl-n-pentyl, 3-methyl-n-pentyl, 2,2-dimethyl-n-butyl, and 2,3-dimethyl-n-butyl.

Among the suitable radicals represented by the basic nitrogen containing radical B are the following:
amino;
(lower alkyl)amino (e.g., N-methylamino);
di(lower alkyl)amino (e.g., N,N-dimethylamino);
(hydroxy lower alkyl)amino;
(hydroxy lower alkyl) (lower alkyl)amino (e.g., N-2-hydroxyethyl-N-methylamino);
di(hydroxy lower alkyl)amino;
phenyl (lower alkyl) amino;
N-phenyl lower alkyl (lower alkyl)amino; and saturated 5- to 7-membered monocyclic heterocyclic radicals of less than twelve carbon atoms, as exemplified by:
piperidino;
(lower alkyl)piperidino;
di(lower alkyl)piperidino;
(lower alkoxy)piperidino;
homopiperidino;
2-, 3-, or 4-piperidyl;
2-, 3-, or 4-(N-lower alkylpiperidyl);
pyrrolidino;
(lower alkyl)pyrrolidino;
di(lower alkyl) pyrrolidino;
(lower alkoxy) pyrrolidino;
2- or 3-pyrrolidyl;
2- or 3-(N-lower alkyl pyrrolidyl);
morpholino;
(lower alkyl)morpholine;
di(lower alkyl)morpholino;
(lower alkoxy)morpholino;
thiamorpholino;
(lower alkyl)thiamorpholino;
di(lower alkyl)thiamorpholino;
(lower alkoxy)thiamorpholino;
piperazino;
4-R-substituted piperazino (e.g., $N^4$-ethylpiperazino, $N^4$-phenylpiperazino, and so forth);

di(lower alkyl)amino- (lower alkyl)piperazyl (e.g., N⁴-dimethylaminoethylpiperazino);
(lower alkyl)-piperazino (e.g., N⁴-methylpiperazino);
di(lower alkyl)piperazino;
(lower alkoxy)piperazino;
homopiperazino;
and 4-R-substituted homopiperazino (e.g., N⁴-benzylhomopiperidino.

The lower alkyl and substituted lower alkyl radicals in the foregoing basic nitrogen containing radicals, B, may contain up to 6 carbon atoms.

The compounds of the invention may be obtained as mixtures of diasteroisomeric compounds when they contain more than one asymmetric atom. Such mixtures of racemates can then be separated into individual racemic compounds.

As to the salts, those coming within the purview of this invention include the acid-addition salts, particularly the pharmaceutically acceptable acid-addition salts, N-oxides and pharmaceutically acceptable acid-addition salts of N-oxides, and pharmaceutically acceptable quaternary ammonium salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic acid, theophylline, 8-chlorotheophylline, p-aminobenzoic, p-acetamidobenzoic, nicotinic, methanesulfonic or cyclohexanesulfamic.

The N-oxide may be formed by dissolving the free base of formula II in a solvent inert to hydrogen peroxide, e.g., ethanol or chloroform, adding excess (on a molar basis) hydrogen peroxide, and allowing the mixture to stand at room temperature for several hours. An acid-addition salt of the N-oxide may be formed by addition of the desired acid, for example, those mentioned above.

The quaternary ammonium salts include those formed with alkyl halides (e.g., methyl chloride, isobutyl bromide, dodecyl chloride and cetyl iodide), benzyl halides (e.g., benzyl chloride) and dilower alkyl sulfates (e.g., dimethyl sulfate).

The compounds of this invention are useful as antiinflammatory agents and are effective in the prevention and inhibition of granuloma tissue formation in warm blooded animals, for example in a manner similar to phenylbutazone or indomethacin. They may be used to decrease joint swelling tenderness, pain and stiffness in mammalian species, e.g., in conditions such as rheumatoid arthritis. The compounds of this invention or a physiologically acceptable acid-addition salt thereof may be compounded according to accepted pharmaceutical practice for administration orally or by injection. Suitable oral dosage forms are tablets, capsules, elixirs, suppositories, or powders, while solutions or suspensions are suitable or injection. The quantity administered may be from about 25 mg to about 2 gm per day, and preferably from about 50 mg to about 200 mg per day.

The following examples illustrate the invention without, however, limiting the same thereto. All temperatures given are in degrees Centigrade unless otherwise stated.

EXAMPLE 1

A. 4-[2-(Dimethylamino)-(Dimethylamino)ethyl]-2H-1,4-benzothiazin-3(4H)-one

A mixture of 108 g of 1,4-benzothiazin-3(4H)-one in 650 ml of DMF is stirred and treated portionwise with 32.5 g of sodium hydride (50% dispersion) while maintaining the temperature below 50°. The solution is then heated to 70°, cooled to 25° and treated with 350 ml of 2.8 N toluene solution of 2-dimethylaminoethyl chloride and 6 g of sodium iodide. This mixture is heated at 100°–105° for 3 hours, cooled, poured into 2 liters of ice-water, and extracted with 500 ml of ether (three times). The organic phases are combined and extracted with a solution of 120 ml of concentrated HCl in 500 ml of water. The aqueous phase is cooled and treated portionwise with 240 g of $K_2CO_3$. The liberated base is extracted with 500 ml of ether (three times), the organic phases are combined, dried ($MgSO_4$), filtered and the solvent evaporated. The residue is fractionated to give 103.5 g of colorless product; b.p. 146°–149° (0.2 mm).

B.
2-Benzoyl-4-[2-(dimethylamino)ethyl]-2H-1,4-benzothiazin-3(4H)-one, hydrochloride A solution of 24 g of the product from part A and 25 ml of methyl benzoate in 100 ml of dimethylsulfoxide (DMSO) is stirred and treated portionwise with 10 g of 50% NaH. About 10 minutes after the completion of the addition, a vigorous reaction occurs, accompanied by considerable foaming and a moderate temperature rise. (The mixture is cooled intermittently to keep the temperature below 30°.) When the reaction has subsided, the mixture is heated at 60°–65° for 2 hours, kept overnight at room temperature, and poured with stirring into 600 ml of ice-water. The pH of the resulting solution is adjusted to 9.0 with 10% acetic acid to give a gummy precipitate. The latter is extracted with chloroform (4 × 200 ml), dried ($MgSO_4$) and the solvent evaporated. The residue (ca. 50 g) is taken up in 500 ml of ether and extracted with a cold solution of 10 ml of concentrated HCl in 120 ml of water, followed by 50 ml of water. The combined aqueous layers are washed with ether, cooled, and basified with 20 g of $K_2CO_3$. The liberated base is extracted with ether (4 × 200 ml), dried ($MgSO_4$), and the solvent evaporated to give 34.4 g of solid, mp 87°–90° (s. 80°). Crystallization from a mixture of 70 ml of benzene and 70 ml of hexane gives 27 g of cream-colored base; mp 88°–90° (s. 80°). The analytical sample is recrystallized from acetonitrile; mp 105°–107°.

A cooled solution of the base (13 g) in 400 ml of ether is treated with 100 ml of ether containing 7 ml of 5.9 N alcoholic HCl to precipitate the hydrochloride as a pale yellow solid. After cooling for 3 hours, the material is collected under nitrogen, washed with ether, and dried in vacuo; wt., 13.2 g (72%); mp 150°–152° (foam); s, 74°. Crystallization from 100 ml of hot acetonitrile gives 9.3 g of colorless product; mp 177°–179°.

EXAMPLE 2

A.

4-[3-(Dimethylamino)propyl]-2H-1,4-benzothiazin-3(4H)-one

The title product is prepared by reacting sixty grams (0.36 mole) of 1,4-benzothiazin-3(4H)-one in 360 of DMF with 18 g (0.37 mole) of 50% NaH, 260 ml (0.55 mole) of a 2.1 N toluene solution of 3-dimethylaminopropyl chloride, and 4 g of sodium iodide according to the procedure described in Example 1, part A; yield, 57.7 g; bp 157°–160°/0.2 mm.

B.

2-Benzoyl-4-[3-(dimethylamino)propyl]-2H-1,4-benzothiazin-3(4H)-one, hydrochloride The product from part A (25 g; 0.1 mole) is reacted with 25 ml (0.2 mole) of methyl benzoate and 10 g (0.2 mole) of 50% NaH in 100 ml of DMSO according to the procedure described in Example 1, part B. The crude solid base (36 g) is crystallized from 50 ml of acetonitrile to give 24.2 g of pale yellow solid; mp 88°–90°.

A cooled solution of 12 g of base in 300 ml of ether is treated with 100 ml of ether containing 4.5 ml of 7.8 N alcoholic HCl to precipitate the solid hydrochloride. After standing in the cold overnight, the latter is collected under nitrogen, washed with ether, and dried in vacuo, wt. 13.4 g (69%); mp 108°–110° (foaming), s. 94°. The material is dissolved in 200 ml of chloroform, Darco-treated, and the solvent evaporated to give a foamy residue which was crystallized from 100 ml of acetone. The material dissolves readily, then a crystalline solid rapidly separates. After cooling overnight, the yield of colorless product is 9.2 g; mp 176°–178°.

EXAMPLE 3

4-[3-(Dimethylamino)propyl]-2-pivaloyl-2H-1,4-benzothiazin-(4H)-one, hydrochloride 4-[3-(Dimethylamino)propyl]-2H-1,4-benzothiazin3(4H)-one (22.5 g) prepared as described in Example 2, part A is reacted with 21 g of methyl pivalate and 9 g of 50% NaH in 100 ml of DMSO as described in Example 1, part B. There is only a slight temperature rise (31°) and no vigorous foaming. The mixture is stirred at 70°–75° for 3 hours, cooled, poured into 600 ml of ice-water, neutralized to pH 8 with AcOH, and extracted with ether (4 × 200 ml). The combined extracts are dried (MgSO$_4$) and the solvent evaporated to give 24 g of oil. The latter is taken up in ether and extracted with a cool solution of 15 ml of concentrated HCl in 250 ml of H$_2$O followed by 50 ml of H$_2$O. The combined aqueous layers are cooled, basified with 30 g of K$_2$CO$_3$, extracted with ether (3 × 150 ml) and the combined extracts dried (MgSO$_4$). Evaporation of the ether gives 18 g of oil.

When a solution of the latter in 70 ml of hexane is "scratched," a crystalline solid separates. After standing in the cold overnight, the base is collected, washed with hexane, and dried; wt., 7.6 g, mp 61°–63°.

A cooled solution of the base (7.4 g) in 20 ml of EtOH is treated with 2.8 ml of 7.7 N alcoholic HCl and diluted to cloudiness with ether (ca. 180 ml). On scratching, the crystalline hydrochloride gradually separates; crude yield after cooling overnight, 6.4 g; mp 148°–150° (s, 125°). The material is slightly hygroscopic. Crystallization from 50 ml of CH$_3$CN gives 5.8 g of nearly colorless, non-hygroscopic solid; mp 234°–236°.

EXAMPLE 4

4-[3-(Dimethylamino)propyl]-2-isonicotinoyl-2H-1,4-benzothiazin-3(4H)-one, hydrochloride Twenty-five grams (0.1 mole) of 4-[3-(dimethylamino)propyl]-2H-1,4-benzothiazin-3(4H)-one prepared as described in Example 2, part A is reacted with 25 ml of methyl isonicotinate and 10 g of 50% NaH in 100 ml of DMSO as described in Example 1, part B. The vigorous reaction is accompanied by considerable foaming even with ice-cooling.

The syrupy base (12.2 g) is taken up in 600 ml of ether, cooled, and treated with 150 ml of ether containing 4.5 ml of 7.7 N alc. HCl to precipitate the hydrochloride as a yellow-orange amorphous solid. After cooling for 3 hours, the latter is collected under N$_2$, washed with ether, and dried in vacuo; wt., 11 g; mp 107°–109° (foaming).

EXAMPLE 5

2-Benzoyl-4-[3-(dimethylamino)propyl]-2H-pyrido[3,2-b][1,4]oxazin-3(4H)-one, hydrochloride

A.

4-[3-(Dimethylamino)propyl]-2H-pyrido[3,2-b-1,4-oxazin-3(4H)-one

Twenty-five grams (0.17 mole) of 2H-pyrido[3,2-b][1,4]-oxazin-3(4H)-one are reacted with 8.5 g (0.18 mole of 50% NaH, 120 ml (0.26 mole) of a 2.2 N toluene solution of 3-dimethylaminopropyl chloride and 2 g of sodium iodide in 170 ml of DMF as described in Example 1, part A; yield, 21 g; bp 131°–133°/0.2 mm.

B.

2-Benzoyl-4-[3-(dimethylamino)propyl]-2H-pyrido[3,2]-[1,4]-oxazin-3(4H)-one, hydrochloride The product from part A (16 g; 0.068 mole) is reacted with 17 ml (0.14 mole) of methyl benzoate, and 7 g (0.14 mole) of 50% NaH in 70 ml of DMSO as described in Example 1, part B. After the addition of the NaH, the mixture is warmed to 30° (warm water bath) to initiate the reaction. The temperature is then kept below 35° by means of intermittent ice-water cooling. The reaction mixture is finally stirred at 70°–75° for 3 hours and kept overnight at room temperature. The yield of oily base is 22.8 g.

A solution of the base (22.5 g) in 600 ml of ether is treated with 100 ml of ether containing 9.2 ml of 7.3 N alcoholic HCl to precipitate the hydrochloride as an oil which gradually crystallizes on seeding (seeds obtained from acetonitrile), rubbing, and cooling; crude yield, 20 g; mp 164°–169°. Crystallization from 70 ml of acetonitrile gives 13.7 g of pale yellow material; mp 178°–180°.

EXAMPLE 6

A.

1-[3-(Dimethylamino)propyl]-1H-pyrido[2,3-b][1,4]thiazin-2(3H)-one

A 50% oil dispersion of NaH (7.8 g; 0.16 mole) is added to a stirred suspension of 26 g (0.16 mole) of 1H-pyrido[2,3-b][1,4]thiazin-2(3H)-one in 525 ml of toluene and the mixture gradually warmed, effervescence occurs at about 90°. After heating to reflux for 45 minutes, the mixture is cooled to 30°, treated with 120 ml (0.22 mole) of a 1.8 N toluene solution of 3-dimethylaminopropyl chloride and refluxed for 4 hours. After standing overnight, the mixture is worked up as described in Example 1, part A, to give 23 g of crude base. This is combined with 10 g of base from an earlier experiment and distilled; yield, 27.3 g; bp. 166°–169°/0.2 mm.

B.
3-Benzoyl-1-[3-(dimethylamino)propyl]-1H-pyrido[2,3-b]-[1,4]thiazin-2(3H)-one, hydrochloride The product from part A (15 g; 0.06 mole) is reacted with 15 ml (0.12 mole) of methyl benzoate and 6.1 g (1.13 mole) of 50% NaH in 65 ml of DMSO as described in Example 1, part B. The yield of oily base is 23.8 g.

A solution of the base in 400 ml of ether is treated with 200 ml of ether containing 8.4 ml of 7.15 N alcoholic HCl to precipitate the solid hydrochloride; crude yield, 22 g; mp 126°–130° (foaming); s. 119°. The material is crystallized from 50 ml of $CH_3CN$ to give 16 g of pale yellow solid; mp 185°–188° (dec).

Following recrystallization from 100 ml of $CH_3CN$, the cream-colored material weighs 11.7 g; mp 190°–192° (dec).

EXAMPLE 7

4-[2-(Dimethylamino)ethyl]-2-(α-hydroxybenzyl)-2H-1,4-benzothiazin-3(4H)-one, hydrochloride The free base from Example 1 (13.3 g) is reacted with 4 g of sodium borohydride in 160 ml of methanol. The viscous product (11.2 g) is triturated with 40 ml of boiling acetonitrile and cooled to give 5 g of base; mp 151°–153°.

The base (4.9 g) is dissolved in a warm mixture of 15 ml of chloroform and 15 ml of methanol, cooled, treated with 2.5 ml of 5.9 N alcoholic HCl, and diluted with ether to precipitate the hydrochloride as a gum which crystallizes on rubbing and cooling; crude yield, 5.0 g; mp 204°–206°. Following crystallization from a mixture of 25 ml of warm methanol and 50 ml of ether, the colorless material weighs 4.6 g; mp 207°–209°.

EXAMPLE 8

4-[3-(Dimethylamino)propyl]-2-(α-hydroxybenzyl)-2H-1,4-benzothiazin-3(4H)-one, hydrochloride The free base from Example 2 (12.3 g) is reacted with 3.6 g of sodium borohydride in 150 ml of methanol. The crude syrupy base (12.1 g) is crystallized from 130 ml of isopropyl ether to give 10 g of solid; mp 105°–107° (s. 100°).

A solution of the base (9.9 g) in 50 ml of chloroform is treated with 3.7 ml of 7.7 N alcoholic HCl and diluted with several volumes of ether to precipitate the hydrochloride as a gum which gradually becomes granular on rubbing and standing in the cold; crude yield, 10.3 g; mp 175°–178°. Following crystallization from 75 ml of acetonitrile, the colorless product weighs 7.9 g; mp 182°–184°.

EXAMPLES 9–12

Following the procedure of Example 6 but substituting for 1H-pyrido[2,3-b][1,4]thiazine-2(3H)-one the starting material shown in Column I, there is obtained the product shown in Column II:

| Example | I | II |
|---|---|---|
| 9 | 1H-pyrido[3,4-b][1,4]-thiazin-2(3H)-one | 3-benzoyl-1-[3-(dimethylamino)propyl]-1H-pyrido[3,4-b][1,4]-thiazin-2(3H)-one |
| 10 | 1H-pyrido[4,3-b][1,4]-thiazin-2(3H)-one | 3-benzoyl-1-[3-(dimethylamino)propyl]-1H-pyrido[4,3-b][1,4]-thiazin-2(3H)-one |
| 11 | 1H-pyrido[3,2-b][1,4]-thiazin-2(3H)-one | 3-benzoyl-1-[3-(dimethylamino)propyl]-1H-pyrido[3,2-b][1,4]-thiazin-2(3H)-one |
| 12 | 5,7-dibromo-1H-pyrido-[4,3-b][1,4]thiazin-2-(3H)-one | 3-benzoyl-1-[3-(dimethylamino)propyl]-5,7-dibromo-1H-pyrido-[4,3-b][1,4]thiazin-2(3H)-one |

EXAMPLES 13–18

Following the procedure of Example 5 but substituting for 2H-pyrido[3,2-b][1,4]oxazin-3(4H)-one the starting material shown in Column I, there is obtained the product shown in Column II:

| Example | I | II |
|---|---|---|
| 13 | 2H-pyrido[2,3-b][1,4]-oxazin-3(4H)-one | 2-benzoyl-4-[3-(dimethylamino)propyl]-2H-pyrido-[2,3-b][1,4]oxazin-3(4H)-one |
| 14 | 2H-pyrido[3,4-b][1,4]-oxazin-3(4H)-one | 2-benzoyl-4-[3-(dimethylamino)propyl]-2H-pyrido-[3,4-b][1,4]oxazin-3(4H)-one |
| 15 | 2H-pyrido[4,3-b][1,4]-oxazin-3(4H)-one | 2-benzoyl-4-[3-(dimethylamino)propyl]-2H-pyrido-[4,3-b][1,4]oxazin-3(4H)-one |
| 16 | 6-methyl-2H-pyrido[3,2-b][1,4]oxazin-3(4H)-one | 2-benzoyl-4-[3-(dimethylamino)propyl]-6-methyl-2H-pyrido-[3,2-b][1,4]oxazin-3(4H)-one |
| 17 | 7-methyl-2H-pyrido-[3,2-b][1,4]oxazin-3(4H)-one | 2-benzoyl-4-[3-(dimethylamino)propyl]-7-methyl-2H-pyrido-[3,2-b][1,4]oxazin-3(4H)-one |
| 18 | 8-methyl-2H-pyrido-[3,2-b][1,4]oxazin-3(4H)-one | 2-benzoyl-4-[3-(dimethylamino)propyl]-8-methyl-2H-pyrido[3,2-b][1,4]oxazin-3(4H)-one |

EXAMPLES 19–32

By reacting a substituted o-aminobenzenethiol of formula III wherein the substituent(s) X is as indicated in Column I with chloroacetic acid, there is obtained the correspondingly substituted benzothiazin-3-one of formula IV as the hydrochloride. Reaction of the latter with the haloalkylene-B compound indicated in Column II following the procedure of Example 1(A) yields the corresponding compound of formula I-1. Reaction of the latter with methyl benzoate following the procedure of Example 1(B) yields the final product of formula II-1 wherein R is phenyl.

| Example | I | | | | II |
|---|---|---|---|---|---|
| | 3 | 4 | 5 | 6 | |
| 19 | H | F | H | H | 2-(amino)ethyl chloride |
| 20 | H | H | H | Cl | 2-(methylamino)ethyl chloride |
| 21 | H | H | Br | H | 2-(diethylamino)ethyl chloride |
| 22 | H | H | CH$_3$ | H | 2-methyl-3-(dimethylamino)-propyl chloride |
| 23 | H | H | H | C$_2$H$_5$ | 6-(dimethylamino)hexyl chloride |
| 24 | H | CF$_3$ | H | H | 2-[N-methyl-N-(2-hydroxyethyl)amino]ethyl chloride |
| 25 | H | H | n-C$_6$H$_{11}$ | H | 2-[bis-N-(2-hydroxyethyl)-amino]ethyl chloride |
| 26 | OH | H | H | H | 3-(benzylamino)propyl chloride |
| 27 | H | SC$_2$H$_5$ | H | H | 3-(N-phenethyl-N-methyl-amino)propyl chloride |
| 28 | H | H | H | NO$_2$ | 2-(piperidino)ethyl chloride |
| 29 | H | CH$_3$SO$_2$ | H | H | 2-(2-methylpiperidino)-ethyl chloride |
| 30 | H | NH$_2$ | CH$_3$ | H | 2-(2,6-dimethylpiperidino)-ethyl chloride |
| 31 | OCH$_3$ | OCH$_3$ | H | H | 2-(2-ethoxypiperidino)-propyl chloride |
| 32 | H | H | N(CH$_3$)$_2$ | H | 2-(hexamethyleneamino)propyl chloride |

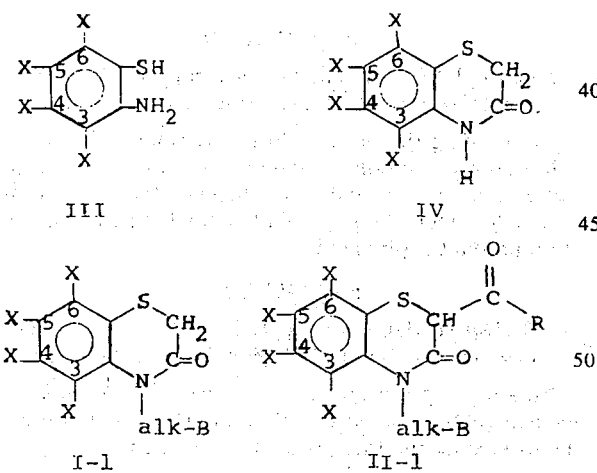

EXAMPLES 33–46

By reacting the compound of formula I-1 indicated in Column I with NaH and the R-acylating agent indicated in Column II according to the procedure of Example 1(B), there is obtained the corresponding compound of formula IIa-1

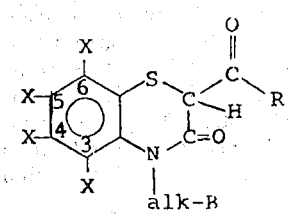

wherein R is the radical indicated in Column III.

| Example | I Compound of formula I-1 of Example | II R-acylating agent | III R |
|---|---|---|---|
| 33 | 19 | methylpropionate | —C$_3$H$_7$ |
| 34 | 20 | methylacetate | —CH$_3$ |
| 35 | 21 | methylhexanoate | —C$_6$H$_{11}$ |
| 36 | 22 | methyloctanoate | —C$_8$H$_{15}$ |
| 37 | 23 | nicotinic acid, methyl ester | pyridyl |
| 38 | 24 | cyclohexane carboxylic acid, methyl ester | cyclohexyl |

| Example | I Compound of formula I-1 of Example | II R-acylating agent | III R |
|---|---|---|---|
| 39 | 25 | pyridine 2-carboxylic acid, methyl ester |  |
| 40 | 26 | phenylacetic acid, methyl ester | 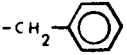 |
| 41 | 27 | thiophene-2-carboxylic acid, methyl ester |  |
| 42 | 28 | furane-2-carboxylic acid, methyl ester |  |
| 43 | 29 | naphthalene-1-carboxylic acid, methyl ester |  |
| 44 | 30 | naphthalene-2-carboxylic acid, methyl ester |  |
| 45 | 31 | o-toluic acid, methyl ester |  |
| 46 | 32 | m-bromobenzoic acid, methyl ester |  |

EXAMPLE 47

4-[3-(Dimethylamino)propyl]-2-(α-propylcinnamoyl)-2H-1,4-benzothiazin-3(4H)-one, fumarate salt, hydrate (1:1:1)

4-[3-(Dimethylamino)propyl]-2H-1,4-benzothiazin-3(4H)-one (22 g; 0.088 mole) is reacted with 36 g (0.18 mole) of methyl α-propylcinnamate and 9 g (0.18 mole) of NaH (50% oil dispersion) in 100 ml of DMSO as described in Example 2 to give 33.7 g of red viscous base. The latter (33.3 g) is mixed with 9.2 g of fumaric acid in 70 ml of MeOH and diluted with several volumes of ether to precipitate the fumarate salt as a red oil.

The solvents are decanted and the product rubbed under fresh quantities of ether until it becomes almost completely granular. The yield of tacky orange solid is 35.5 g (72%). The material is then dissolved in 150 ml of CHCl₃ and added dropwise to 1.8 liters of vigorously stirred ether to give 25.8 g (53%) of completely granular, yellow, solid; mp 100°–102° (s. 80°).

A sample of the fumarate is treated with K₂CO₃ to give the base as a brittle orange solid; mp 73°–75° (s. 64°).

EXAMPLE 48

2-Benzoyl-4-[2-(dimethylamino)ethyl]-2H-1,4-benzothiazin-3(4H)one-1-oxide, hydrochloride By treating the product from Example 1(B) with an equivalent quantity of H₂O₂ in dilute acetic acid and allowing the mixture to stand overnight, the title product is obtained.

EXAMPLE 49

2-Benzoyl-4-[3-(dimethylamino)propyl]-2H-1,4-benzothiazin-3(4H)-one-1-oxide, hydrochloride By treating the product from Example 2 (B) with a chloroform solution containing 1 equivalent of m-chloroperbenzoic acid and allowing the mixture to stand for about two hours at room temperature, the title product is obtained.

EXAMPLE 50

4-[3-(Dimethylamino)propyl]-2-pivaloyl-2H-1,4-benzothiazin-3(4H)-one-1,1-dioxide, hydrochloride By refluxing the product from Example 3 with two equivalents of a chloroform solution of m-chloroperbenzoic acid, the title product is obtained.

EXAMPLES 51–74

Following the procedure of Example 49 but substituting, respectively, for the product of Example 2(B) the final product of Examples 4, 6, 9, 11, 12, 19, 20, 22, 24, 25, 26, 27, 28, 29, 30, 32, 33, 34, 37, 38, 40, 41, 43 and 46, there is obtained respectively, the corresponding sulfoxide.

EXAMPLES 75–92

Following the procedure of Example 50 but substituting, respectively, for the product of Example 3, the final product of Examples 6, 10, 12, 19, 22, 24, 25, 28, 29, 30, 31, 33, 35, 39, 40, 42, 44 and 45, there is obtained, respectively, the corresponding sulfone.

EXAMPLE 93

2-Benzoyl-4-[2-(dimethylamino)ethyl]-2H-1,4-benzothiazin-3(4H)-one, hydrochloride By heating the sodium salt of o-nitrophenol with an equimolar amount of chloroacetic acid at 60°C for 2 hours, followed by catalytic reduction of the nitro group by Pd-C (causing spontaneous cyclization), there is obtained benzoxazin-3(4H)-one hydrochloride. Reaction of the latter with 2-dimethylaminoethyl chloride following the procedure described in Example 1(A) yields 4-[2-(dimethylamino)ethyl]-2H-1,4-benzothiazin-3(4H)-one. A solution of the latter compound is reacted with methyl benzoate following the procedure described in Example 1(B) to yield the title product.

EXAMPLES 94–124

Following the procedure of Example 93 but substituting for o-nitrophenol wherein the substituents in the 3-, 4-, 5- or 6-positions are as indicated in Column I, and substituting for 2-dimethylaminoethyl chloride the chloride of the alk-B radical indicated in Column II, and substituting for methyl benzoate the ester of the formula

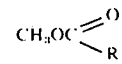

wherein R is as indicated in Column III, there is obtained the compound of formula IIa-2 of the following formula wherein the $X_m$, alk-B and R substituents are as indicated, respectively, in Columns I, II and III:

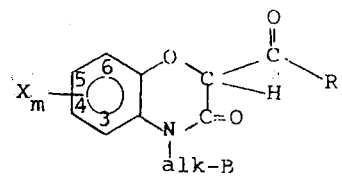

I

| | I | | | II | III |
|---|---|---|---|---|---|
| 3 | 4 | 5 | 6 | alk-B halide | R |
| 94 | | Cl | | Cl | 2-(2-piperidyl)ethyl | ⟨C₆H₄-CH₃⟩ |
| 95 | Br | | Br | | 3-(3-piperidyl)propyl | ⟨C₆H₄-CH₃⟩ |
| 96 | CH₃ | | | | 2-(4-piperidyl)ethyl | ⟨C₆H₄-Cl⟩ |
| 97 | | | CF₃ | | 2-(1-methyl-2-piperidyl)ethyl | ⟨C₆H₃(NO)(NO₂)⟩ |
| 98 | | | n-C₃H₇ | | 3-(1-methyl-3-piperidyl)propyl | ⟨C₆H₃(NO₂)₂⟩ |
| 99 | | | | Cl | 4-(1-methyl-4-piperidyl)butyl | ⟨C₆H₄-OH⟩ |
| 100 | | F | | | 3-(pyrrolidino)propyl | ⟨C₆H₄-OH⟩ |
| 101 | | | | CH₃ | 2-(2-methyl-pyrrolidino)ethyl | ⟨C₆H₄-OH⟩ |
| 102 | | | OCH₃ | | 2-(2,5-dimethyl-pyrrolidino)ethyl chloride | ⟨C₆H₄-NH₂⟩ |
| 103 | Cl | Cl | Cl | Cl | 3-(3-ethoxy-pyrrolidino)propyl | ⟨C₆H₄-NH₂⟩ |

3,984,405

-continued

| | I | | | II | III |
|---|---|---|---|---|---|
| | 3 | 4 | 5 | 6 | alk-B halide | R |

| | 3 | 4 | 5 | 6 | alk-B halide | R |
|---|---|---|---|---|---|---|
| 104 | | Br | | | 2-(2-pyrrolidyl)ethyl | 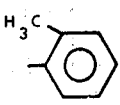 |
| 105 | | Br | | Br | 2-(3-pyrrolidyl)ethyl | 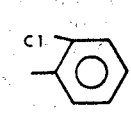 |
| 106 | | SC₂H₅ | | | 2-(N-methyl-2-pyrrolidyl)ethyl | 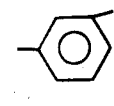 |
| 107 | | Br | | Br | 3-(N-methyl-3-pyrrolidyl)propyl | 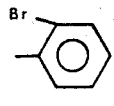 |
| 108 | | Br | | CH₃ | 2-(morpholino)ethyl | 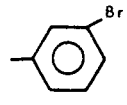 |
| 109 | CH₃ | | | | 3-(2-methylmorpholino)-propyl | 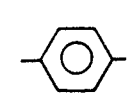 |
| 110 | CH₃ | | | | 3-(2,6-dimethyl-morpholino)propyl | 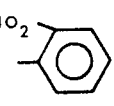 |
| 111 | | | CH₃ | | 3-(3-methoxy-morpholino)propyl | 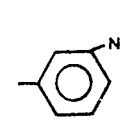 |
| 112 | CH₃ | | | Cl | 2-(thiamorpholino)-ethyl | 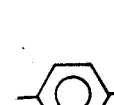 |
| 113 | CH₃ | | | Br | 3-(piperazino)ethyl | 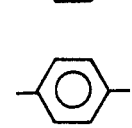 |
| 114 | N(H)(CH₃) | | | | 3-(4-methyl-piperazino)propyl |  |
| 115 | | | Cl | | 3-(4-cyclohexyl-piperazino)propyl | 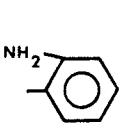 |
| 116 | | | F | | 3-(4-phenyl-piperazino)propyl | 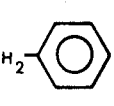 |

| | I | | | II | III |
|---|---|---|---|---|---|
| | 3 | 4 | 5 | 6 | alk-B halide | R |
| 117 | | SO$_2$CH$_3$ | | | 2-(4-benzyl-piperazino)ethyl | 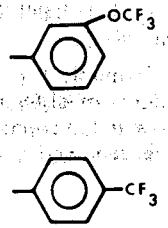 |
| 118 | | N(CH$_3$)$_2$ | | | 3-(4-phenethyl-piperazino)propyl | 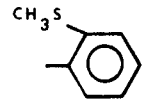 |
| 119 | | C$_2$H$_5$ | | | 3-[4-dimethylamino-ethyl)piperazino]propyl | 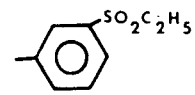 |
| 120 | | OC$_2$H$_5$ | | | 3-(2-methyl-piperazino)propyl | 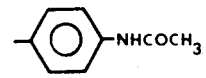 |
| 121 | | O-n-C$_6$H$_{11}$ | | | 3-(2,6-dimethyl-piperazino)propyl | 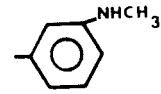 |
| 122 | CH$_3$ | | | | 3-(3-methoxy-piperazino)propyl | 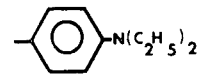 |
| 123 | CH$_3$ | | | | 2-(morpholino)ethyl | 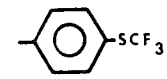 |
| 124 | CH$_3$ | | | | 3-(piperazino)ethyl |  |

EXAMPLE 125

3-Benzoyl-1-[2-(dimethylamino(ethyl]indolin-2-one, hydrochloride

Utilizing the procedure of example 1 but substituting indolin-2-one for 1,4-benzothiazin-3(4H)-one in part A, the title product is prepared.

EXAMPLE 126

3-Benzoyl-1-[2-(dimethylamino)ethyl]-5-bromoindolin-2-one, hydrochloride

Following the procedure of example 125 but substituting 5-bromoindolin-2-one for indolin-2-one, the title product is obtained.

EXAMPLE 127

4-[2-(Dimethylamino)ethyl]-α-methyl-α-phenyl-2H-1,4-benzothiazin-2-methanol, hydrochloride Interaction of the free base of the product of example 1 with 1 equivalent of CH$_3$MgBr in ether at room temperature forms a Grignard complex which is decomposed with ice water and the ethereal solution dried over anhydrous MgSO$_4$, filtered and the filtrate treated with anhydrous HCl to yield the title product.

EXAMPLE 128

2-(p-amino)Benzoyl-4-[2-(2,5-dimethylpyrrolidino)ethyl]-5-hydroxy-2H-1,4-benzoxazin-3(4H)-one, hydrochloride By heating the product of example 102 in the presence of excess pyridine HCl at 100°C for 1 hour, the title product is obtained.

EXAMPLE 129

2-Furyl-4-[2-(piperidino)ethyl]-6-acetylamino-2H-1,4-benzothiazin-3(4H)-one, hydrochloride By hydrogenating the 6-nitro product of example 42 in the presence of Pd-C and acylating the resulting 6-amino compound with 1 mole of acetyl chloride in chloroform, the title product is obtained.

EXAMPLE 130

2-Benzoyl-4-[2-(dimethylamino)ethyl]-2H-1,4-benzothiazine-3(4H)-one, methobromide A solution of the free base of Example 1 in acetonitrile is treated with two equivalents of methyl bromide and the solution allowed to stand at room temperature for 8 hours. The solvent is removed to give the product.

EXAMPLE 131

2-Benzoyl-4-[2-(dimethylamino)ethyl]-2H-1,4-benzothiazine-3(4H)-one, N-oxide

A solution of the free base of Example 1 in acetonitrile is treated with two equivalents of $H_2O_2$ in acetic acid and the solution allowed to stand at room temperature for 8 hours. The solvent is removed to give the product.

What is claimed is:

1. A compound selected from the group consisting of 2-benzoyl-4-[3-(dimethylamino)propyl]-2H-pyrido[3,2-b][1,4]oxazin-3(4H)-one, 2-benzoyl-4-[3-(dimethylamino)propyl]-2H-pyrido-[2,3-b][1,4]oxazin-3(4H)-one, 2-benzoyl-4-[3-(dimethylamino)propyl]-2H-pyrido]3,4-b][1,4]oxazin-3(4H)-one, and 2-benzoyl-4-[3-(dimethylamino)propyl]-2H-pyrido]4,3-b][1,4]oxazin-3(4H)-one, and pharmaceutically acceptable acid addition salts thereof.

2. A compound as defined in claim 1 having the name 2-benzoyl-4-[3-(dimethylamino)propyl]-2H-pyrido[3,2-b][1,4]-oxazin-3(4H)-one, hydrochloride.

* * * * *

UNITED STATES PATENT AND TRADEMARK OFFICE
CERTIFICATE OF CORRECTION

PATENT NO. : 3,984,405
DATED : October 5, 1976
INVENTOR(S) : John Krapcho

It is certified that error appears in the above-identified patent and that said Letters Patent are hereby corrected as shown below:

Column 3, structure I-1 should read

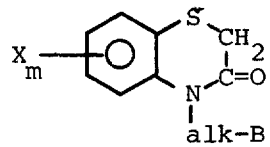

Column 3, structure I-9 should read

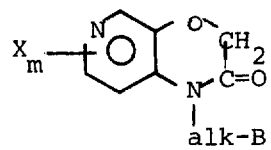

Column 5, line 5, "II-1" should read --IIa-1--.
Column 10, line 58, "(lower alkyl)morpholine" should read --(lower alkyl)morpholino--.
Column 12, lines 3 and 4 should read --A. 4-[2-(Dimethylamino)-ethyl]-2H-1,4-benzothiazin- --.
Column 13, line 47, "thiazin3" should read --thiazin-3--.
Column 14, line 31, "[3,2-b" should read --[3,2-b]--.
Column 14, line 36, after "mole" insert --)--.
Example 97, column III, the structure should read

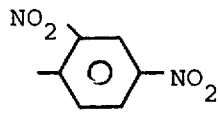

Column 25, line 48, "(dimethylamino(" should read --(dimethylamino)--.
Column 28, line 6, "]3,4-b]" should read --[3,4-b]--.
Column 28, line 8, "]4,3-b]" should read --[4,3-b]--.

Signed and Sealed this

Twenty-eighth Day of December 1976

[SEAL]

Attest:

RUTH C. MASON
Attesting Officer

C. MARSHALL DANN
Commissioner of Patents and Trademarks